United States Patent
Lee et al.

(10) Patent No.: US 9,279,783 B2
(45) Date of Patent: Mar. 8, 2016

(54) APPARATUS FOR DETECTING CRACK USING HETEROGENEOUS MAGNETIC SENSORS

(71) Applicant: INDUSTRY-ACADEMIC COOPERATION FOUNDATION CHOSUN UNIVERSITY, Gwangju (KR)

(72) Inventors: Jin Yi Lee, Gwangju (KR); Jong Woo Jun, Gwangju (KR); Jung Min Kim, Gwangju (KR)

(73) Assignee: INDUSRTY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 515 days.

(21) Appl. No.: 13/667,086

(22) Filed: Nov. 2, 2012

(65) Prior Publication Data
US 2013/0314084 A1 Nov. 28, 2013

(30) Foreign Application Priority Data
May 22, 2012 (KR) ........................ 10-2012-0053987

(51) Int. Cl.
G01R 33/02 (2006.01)
G01R 33/07 (2006.01)
B82Y 25/00 (2011.01)
(Continued)

(52) U.S. Cl.
CPC .............. *G01N 27/82* (2013.01); *G01R 33/072* (2013.01); *G01R 33/091* (2013.01)

(58) Field of Classification Search
None
See application file for complete search history.

(56) References Cited

U.S. PATENT DOCUMENTS

2009/0027048 A1* 1/2009 Sato et al. ...................... 324/247
2009/0315547 A1* 12/2009 Abwa et al. ..................... 324/244
(Continued)

FOREIGN PATENT DOCUMENTS

JP      2006-220621 A      8/2006
KR       10-1094667 B1     3/2011
KR    10-2012-0010051 A    2/2012

OTHER PUBLICATIONS

J. Lee et al., Solid-State Bobbin-Type Hall Sensor Arrays with High Spatial Resolution for Inspecting Cracks in a Small-Bore Piping System, Poster Session ET09 at IEEE International Magnetic Conference 2012, Vancouver, Canada, May 7-11, 2012.
(Continued)

*Primary Examiner* — Melissa Koval
*Assistant Examiner* — Courtney McDonnough
(74) *Attorney, Agent, or Firm* — The PL Law Group, PLLC

(57) ABSTRACT

Disclosed herein are an apparatus and a method for detecting a crack. The apparatus includes a power supply unit, a sensor module, and a signal reception module. The power supply unit supplies power. The sensor module receives the input power from the power supply unit, and outputs sensing power corresponding to the magnetic field of an object to be measured. The signal reception unit converts the sensing power output from the sensor module into a quantitative value, and computes the distribution of the magnetic field. The sensor module includes a first sensor array configured to detect magnetic field vectors in a direction vertical to a sensor surface, and a second sensor array placed on the first sensor array in an overlapping manner and configured to detect magnetic field vectors in a direction lateral with respect to the sensor surface.

16 Claims, 10 Drawing Sheets

(51) Int. Cl.
   *G01N 27/82*    (2006.01)
   *G01R 33/09*    (2006.01)

(56) References Cited

U.S. PATENT DOCUMENTS

2010/0042336 A1* 2/2010 Lee et al. ............... 702/38
2010/0174497 A1* 7/2010 Masuda .................. 702/57

OTHER PUBLICATIONS

J. W. Jun et al., Solid-State Bobbin-Type Hall Sensor Arrays with High Spatial Resolution for Inspecting Cracks in a Small-Bore Piping System, Proceedings of APCF5-MM 2012, Paper No. 169, pp. 258-259.

J Lee et al., Eddy Current Imager Using Bobbin-Type Hall Sensor Arrays for NDE in Small-Bore Piping System, Abstracts: Review of Progress in Quantitative NDE, Denver Colorado, Jul. 15-20, 2012, p. 170.

J Lee et al., 3-D Magnetic Vector Field Camera Using Integrated Hall and MR sensor Arrays, EMSA 2012: 9th European Magnetic Sensors & Actuators Conference: Book of Abstracts, p. 29-30.

Office action Document from Korean Intellectual Property Office (KIPO) dated on Sep. 23, 2013.

Integration of Hall and Giant Magnetoresistive Sensor Arrays for Real-Time 2-D Visualization of Magnetic Field Vectors, IEEE, May 7 to 11, 2012.

* cited by examiner

APPARATUS FOR DETECTING CRACK USING HETEROGENEOUS MAGNETIC SENSORS

CROSS REFERENCE TO RELATED APPLICATIONS AND CLAIM OF PRIORITY

This patent application claims priority to Korean Patent Application number 10-2012-0053987, filed on May 22, 2012, entire contents of which are incorporated herein by reference.

BACKGROUND

1. Field of the Invention

The present invention relates to an apparatus for detecting a crack.

2. Description of the Related Art

Nondestructive testing (NDT) using a magnetic phenomenon is a method that is useful for detecting a surface defect in a structure, a backside defect near the surface of a structure, and an inner side defect near the surface of a structure. Using nondestructive testing, defects of large-scale plants and structures that are used in nuclear power generation, steam power generation and the chemical industry can be detected.

Conventional methods of detecting defects using the distribution of a magnetic field may be classified into a method of performing a two-dimensional (2D) scan using a single magnetic sensor, a method for performing a one-dimensional (1D) scan using sensors arranged in a single column, and a method of using sensors arranged in two dimensions.

The method of performing a 2D scan using a single magnetic sensor requires a longer period of time. The method for performing a 1D scan using sensors arranged in a single column requires separate scan equipment, and also requires that the scan equipment have high precision. The method of using sensors arranged in two dimensions has the advantage of measuring the distributions of a magnetic field at one time. However, the method of using sensors arranged in two dimensions has limited ability to quantitatively evaluate the size of a defect using the leakage of a magnetic field around the defect because single-axis magnetic sensors having magnetic sensitivity are arranged to perform the method.

Furthermore, a conventional method of measuring the distributions of the magnetic field of an object to be measured using tri-axial magnetic sensors limits its spatial resolution because a large number of wires are required.

SUMMARY

Accordingly, one or more embodiments of the present invention has been made keeping in mind the above problems occurring in the prior art, and an aspect of the present invention is to provide an apparatus for detecting a crack, which is capable of rapidly measuring the distribution of the magnetic field of an object to be measured in the direction vertical to a sensor surface and the distribution of the magnetic field in the direction lateral with respect to the sensor surface at high spatial resolution, thereby obtaining 2D and 3D distributions of the magnetic field.

An aspect of the present invention provides an apparatus for detecting a crack, including a power supply unit to supply power; a sensor module to receive the power from the power supply unit and output detected signals corresponding to a magnetic field of an object to be measured, the sensor module including a first sensor array to detect magnetic field vectors in a direction vertical to a sensor surface and a second sensor array overlapped with the first sensor array to detect magnetic field vectors in a direction lateral with respect to the sensor surface; and a signal reception unit to convert the detected signals output from the sensor module into a quantitative value and compute a distribution of the magnetic field.

The first sensor array may include a plurality of magnetic sensors arranged in a matrix with M (a natural number) rows and N (a natural number) columns; and each of the magnetic sensors may include first and second input terminals to receive the power input from the power supply unit and first and second output terminals to output the detected signals.

The apparatus may further include a first input switch unit arranged between the power supply unit and the first input terminal to selectively supply the power input from the power supply unit to the first input terminal; and a second input switch unit arranged between the second input terminal and the ground to selectively apply ground to the second input terminal.

The first input switch unit may include a plurality of switching elements, one terminal of each of which is connected to the first input terminals of the magnetic sensors arranged in a corresponding row and the other terminal of each of which is connected to the power supply unit.

The second input switch unit may include a plurality of switching elements, one terminal of each of which is connected to second input terminals of magnetic sensors arranged in a corresponding row and a remaining terminal of each of which is connected to the ground.

The first and second input switch units may be formed in a row direction, and each include switching elements whose number is equal to a number of magnetic sensors arranged in each row.

The apparatus may further include a switch control unit that applies a first control signal that sequentially turns the plurality of switching elements of the first input switch unit on and off and a second control signal that sequentially turns the plurality of switching elements of the second input switch unit on and off.

The magnetic sensors may be Hall sensors.

The second sensor array may include a plurality of magneto-resistive sensors arranged in a matrix with I (a natural number) rows and J (a natural number) columns; and each of the magneto-resistive sensors may include first and second input terminals to receive the power input from the power supply unit and first and second output terminals to output the detected signals.

The apparatus may further include a third input switch unit arranged between the power supply unit and the first input terminal of each of the magneto-resistive sensors to selectively supply the power input from the power supply unit to the first input terminal; and a fourth input switch unit arranged between the second input terminal of each of the magneto-resistive sensors and the ground power to selectively apply ground power to the second input.

The third input switch unit may include a plurality of switching elements, one terminal of each of which is connected to the first input terminals of the magneto-resistive sensors arranged in a corresponding row and the other terminal of each of which is connected to the power supply unit.

The fourth input switch unit may include a plurality of switching elements, one terminal of each of which is connected to the second input terminals of the magneto-resistive sensors arranged in a corresponding row and the other terminal of each of which is connected to the ground.

The third and fourth input switch units may be formed in a row direction, and each include switching elements whose number is equal to a number of magneto-resistive sensors arranged in each row.

The apparatus of claim may further include a switch control unit to apply a third control signal that sequentially turns the plurality of switching elements of the third input switch unit on and off, and to apply a fourth control signal that sequentially turns the plurality of switching elements of the fourth input switch unit on and off.

The apparatus may further include a plurality of interchange switch units having first terminals thereof fixed to the magneto-resistive sensors, and to be switched to select second and third terminals, thereby interchanging the input and output terminals of the magneto-resistive sensors with each other. Here, the plurality of interchange switch units may include a first interchange switch unit having second terminals connected to the third input switch unit and third terminals connected to the first output terminals; a second interchange switch unit having second terminals connected to the fourth input switch unit and third terminals connected to the second output terminals; a third interchange switch unit having second terminals connected to the first output terminals and third terminals connected to the third input switch unit; and a fourth interchange switch unit having second terminals connected to the second output terminals and third terminals connected to the fourth input switch unit.

When the switching elements of the first to fourth interchange switch units are switched to connect the first and second terminals with each other, the second sensor array may measure the distribution of the magnetic field of the object to be measured in an x-axis direction; and when the switching elements of the first to fourth interchange switch units are switched to connect the first and third terminals with each other, the second sensor array may measure a distribution of the magnetic field of the object to be measured in a y-axis direction.

The switch control unit may provide a fifth control signal that switches the switching elements of the first to fourth input switch units.

Each of the magneto-resistive sensors may be any one of a magneto-resistive (MR) sensor, a giant magneto-resistive (GMR) sensor, a giant magneto-impedance (GMI) sensor, a spin dependent tunneling (SDT) sensor, and a magnetic tunnel junction (MTJ) sensor.

The signal reception unit may include an amplification unit to amplify output applied by the sensor module or a conversion unit configured to convert the output into a digital signal.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Figure 1:
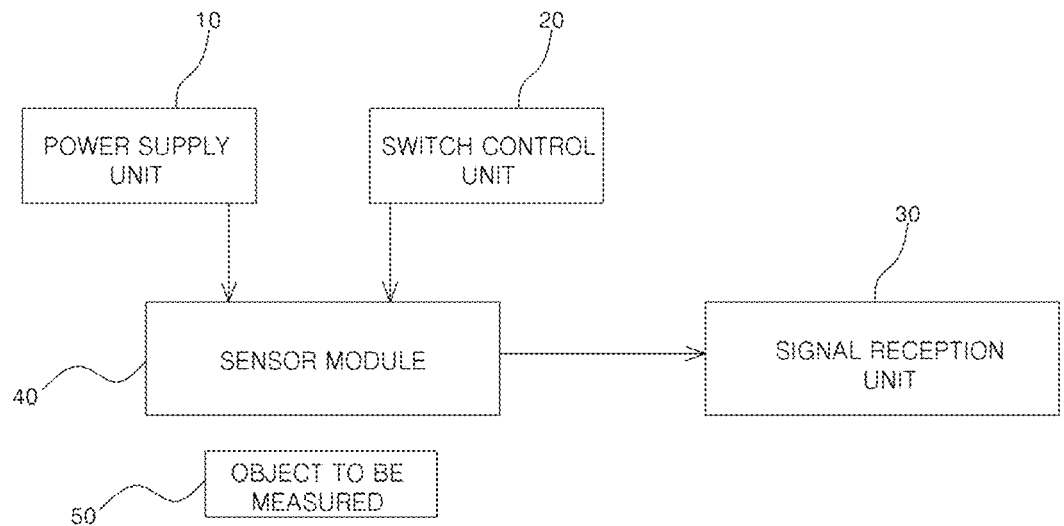
FIG. 1 is a block diagram schematically showing an apparatus for detecting a crack using magnetic sensors according to an embodiment of the present invention.

The present invention is not limited to specific embodiments, but may be subject to a variety of modifications and additions and have a variety of embodiments. Furthermore, it should be appreciated that the present invention includes all modifications, equivalents, and replacements that pertain to the technical scope and spirit of the present.

Although the terms "first," "second," "third," etc. may be used herein to describe various elements and/or components, these elements and/or components should not be limited by these terms. These terms may be only used to distinguish one element and/or component from another element and/or component.

Throughout the overall specification, the same reference numerals are used to designate the same or similar components.

Unless the context otherwise clearly indicates, terms used in the singular include the plural. Furthermore, it should be appreciated that the terms "comprise," "include," and "have" are intended to specify the presence of features, numbers, steps, operations, components, parts, or combinations thereof, but it should not be appreciated that the terms are not intended to exclude the presence of or the possibility of addition of one or more features, numbers, steps, operations, components, parts, or combinations thereof.

Embodiments of the present invention will be described in detail below with reference to FIGS. 1 to 18.

Figure 2:
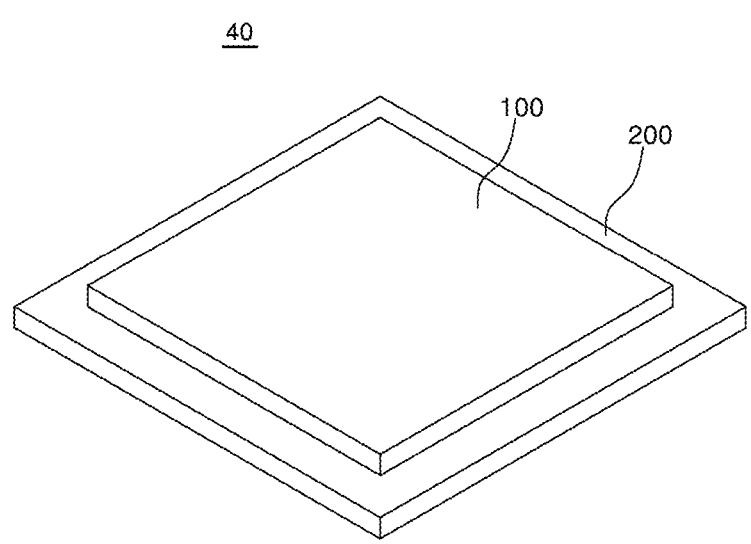
FIG. 2 is a diagram showing an example of the sensor module of FIG. 1.

FIG. 1 is a block diagram schematically showing an apparatus for detecting a crack according to an embodiment of the present invention, and FIG. 2 is a diagram showing an example of the sensor module of FIG. 1.

Referring to FIGS. 1 and 2, the apparatus for detecting a crack according to this embodiment of the present invention may include a power supply unit 10, a switch control unit 20, a sensor module 40, and a signal reception unit 30.

More specifically, the power supply unit 10 may generate DC voltage and/or AC voltage, and supply the voltage to the sensor module 40. In this embodiment, a description thereof will be given with a case in which DC voltage is supplied taken as an example. The power supply unit 10 may supply DC voltage VCC of a predetermined level to the sensor module 40.

The switch control unit 20 may provide on and off signals to a plurality of switches included in the sensor module 40. The switch control unit 20 may provide a first control signal that selectively turns on or off a plurality of switches included in the first sensor array 100 of the sensor module 40 and a second control signal that selectively turns on or off a plurality of switches included in the second sensor array 200 of the sensor module 40.

The first and second control signals may be pulse signals that turn on the switching elements, and be supplied for a period of time that is sufficient for all of the sensors provided in the sensor module 40 to be activated.

The sensor module 40 may output power corresponding to the magnetic field of an object 50 to be measured. Here, the sensor module 40 may detect and output magnetic field vectors in the vertical direction of a sensor surface and magnetic field vectors in the lateral direction of the sensor surface.

The sensor module 40 may be configured such that the first and second sensor arrays 100 and 200 can overlap each other. Here, any one of the sensor arrays may measure magnetic field vectors in the vertical direction of the sensor surface, and the other sensor array may measure magnetic field vectors in the lateral direction thereof. This enables the apparatus for detecting a crack to obtain the 2D or 3D magnetic field vector distribution data of the object 50 to be measured.

The signal reception unit 30 may receive sensing powers from the sensor module 40, and convert the sensing powers into quantitative values. The signal reception unit 30 may convert the power signals received from the sensor module 40 into the distribution of a magnetic field, and output the obtained data.

A signal amplification unit may be further included between the signal reception unit 30 and the sensor module 40.

The signal amplification unit may amplify signals received from the sensor module 40, and provide the amplified signals to the signal reception unit 30. The signal amplification unit may include an overvoltage limiter therein, and amplify input voltages. The signal amplification unit may include a first amplification circuit unit for amplifying a signal received from the first sensor array 100 and a second amplification circuit unit for amplifying a signal received from the second sensor array 200.

Figure 4:
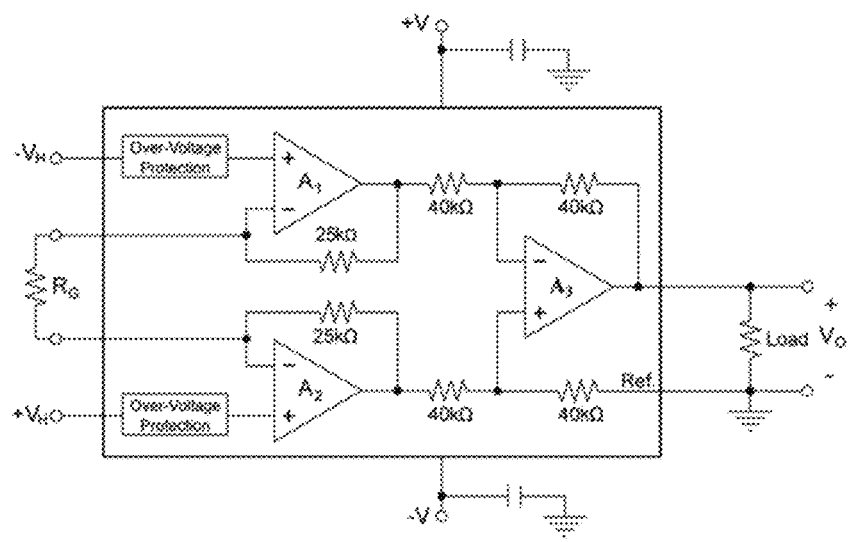
FIG. 4 is a circuit diagram showing an example of a signal amplification unit included in the signal reception unit shown in FIG. 1.

In this embodiment of the present invention, the amplification circuit shown in FIG. 4 may be used as the signal amplification unit, and the amplification circuit may vary depending on the magnitude and sensitivity of signals.

The signal reception unit 30 may further include at least one analog-digital converter for performing signal processing on signals received from the sensor module 40 and converting the signals into digital signals. The analog-digital converter may include analog-digital converters whose number corresponds to the number of the first and second sensor arrays provided in the sensor module 40, or may sequentially convert signals using a single analog-digital converter.

FIGS. 3 to 15 are diagrams showing the sensor module of FIGS. 1 and 2 according to the first embodiment of the present invention.

Referring to FIGS. 3 to 15, the sensor module according to the first embodiment of the present invention may include the first sensor array 100 and the second sensor array 200. In the first embodiment of the present invention, a case in which Hall sensors 110 are arranged in the first sensor array 100 and giant magneto-resistance (GMR) sensors are arranged in the second sensor array 200 will be described as an example.

Figure 3:
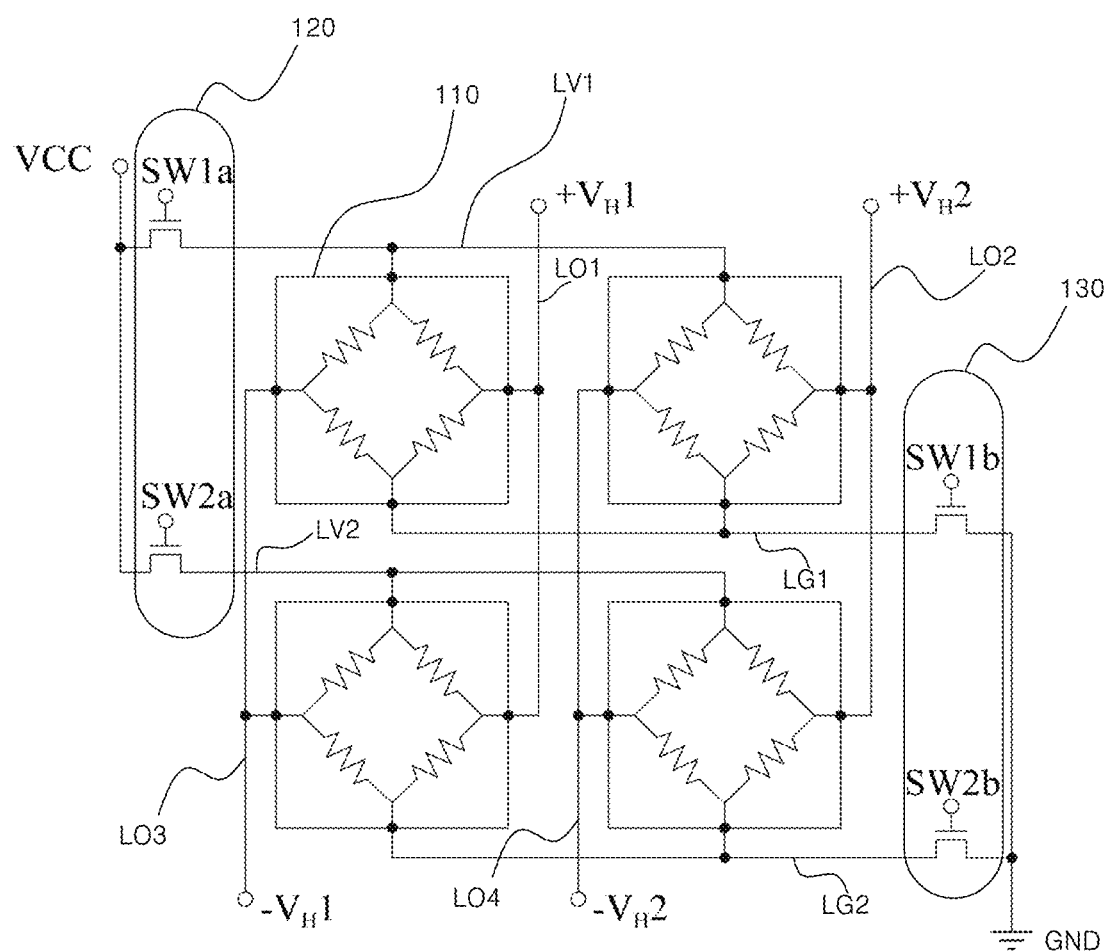
FIG. 3 is a circuit diagram showing the first sensor array of the sensor module shown in FIG. 1.

The first sensor array 100 may measure the vertical magnetic field vector components of the object to be measured. That is, the first sensor array 100 may measure magnetic field vector components distributed in the vertical direction of a sensor surface. For this purpose, the first sensor array 100 may include a plurality of Hall sensors 110, a plurality of power lines LV1 and LV2, a plurality of ground lines LG1 and LG2, a first input switch unit 120, a second input switch unit 130, and a plurality of output lines LO1 to LO4. Although 2×2 Hall sensors 110 are shown in FIG. 3 for convenience of illustration, the number of Hall sensors 110 may vary depending on the design or use thereof. Accordingly, the numbers of switches, power lines and output lines of each of the first and second input switch units 120 and 130 may vary.

Each of the Hall sensors 110 may include four input and output terminals. That is, the Hall sensor 110 may each include first and second input terminals and first and second output terminals. The Hall sensors 110 may be arranged in a matrix with M (a natural number) rows and N (a natural number) columns. However, the Hall sensors 110 are not limited thereto, but may be arranged in a variety of arrangements in order to uniformly measure the vertical magnetic field vector components of an object to be measured.

Here, the output of each of the Hall sensors 110 may be expressed by the following Equation 1:

$$V_Z = k \times B_Z \times I \tag{1}$$

where $V_Z$ is the output of the Hall sensor, k is a Hall constant, I is input current, and $B_Z$ is the intensity of a magnetic field in the z-axis direction.

As shown in Equation 1, the output of the Hall sensor is proportional to the intensity of the external magnetic field in the z-axis direction vertical to the sensor surface.

The power lines LV1 and LV2 are formed in parallel in the row direction. Each of the power lines VL1 and LV2 is connected to the first input terminals of M Hall sensors that are arranged in the row direction. The power lines LV1 and LV2 may provide input power VCC to the Hall sensors 110 arranged in the row direction when any one switching element of the first input switch unit 120 is turned on.

The ground lines LG1 and LG2 are formed in parallel in the row direction. Each of the ground lines LG1 and LG2 is connected to the second input terminals of M Hall sensors that are arranged in the row direction. The ground lines LG1 and LG2 may provide ground GND to the Hall sensors in the row direction when any one switching element of the second input switch unit 130 is turned on.

The first input switch unit 120 may include a plurality of switching elements SW1a and SW2a that are connected to the power lines LV1 and LV2, respectively. The first input switch unit 120 is sequentially turned on in response to the first control signal, and sequentially connects the power supply unit 10 to the power lines LV1 and LV2.

The second input switch unit 130 may include a plurality of switching elements SW1b and SW2b that are connected to the ground lines LG1 and LG2, respectively. The second input switch unit 130 is sequentially turned on in response to the second control signal, and sequentially connects the power supply unit 10 to the ground lines LG1 and LG2.

A plurality of output lines LO1 to LO4 is formed in parallel in the column direction. Each of the first and second output lines LO1 and LO2 is connected to the first output terminals of N Hall sensors 110 that are arranged in the column direction. Each of the third and fourth output lines LO3 and LO4 is connected to the second output terminals of N Hall sensors that are arranged in the column direction.

Here, the first switching element SW1*a* of the first input switch unit 120 may be turned on and off in the same manner as the first switching element SW1*b* of the second input switch unit 130. Accordingly, power voltage VCC and ground voltage GND may be applied to Hall sensors arranged in the first row so that sensing signals +VH1 and −VH1 can be output.

As described above, when the first and second input switch units 120 and 130 are provided, a maximum of 2×(M+N) wires are required, so that the concentration of input or output lines outside the first sensor array 100 can be prevented, with the result that a large number of Hall sensors can be arranged, thereby increasing resolution.

Meanwhile, when the first and second output terminals of Hall sensors 110 arranged in the column direction are connected in common, the intensity of the magnetic field of a specific Hall sensor may be measured.

The second sensor array 200 may measure the lateral magnetic field vector components of the object to be measured. That is, the second sensor array 200 may measure magnetic field vector components distributed laterally with respect to the sensor surface. Here, the magnetic field vector components distributed laterally is divided in the x-axis direction and in the y-axis direction, and then measured. The second sensor array 200 has the same structure as the sensor array 100 except that the former uses magneto-resistive sensors instead of Hall sensors. The second sensor array 200 may include magneto-resistive sensors that are arranged in I (a natural number) rows and J (a natural number) columns. Here, a case in which GMR sensors are used as the magneto-resistive sensors will be described as an example.

The GMR sensors may each have an equivalent circuit that is identical to the equivalent circuit shown in FIG. 3. The GMR sensors are sensitive to the distribution of a magnetic field in the lateral direction, unlike Hall sensors. That is, the GMR sensors can detect magnetic field vectors in the x- and y-axis directions of the sensor surface. The GMR sensors may each include two input pins and two output pins. In each of the GMR sensors, input power is applied to the two input pins, and voltage is output via the two output pins. Here, in the second sensor array 200, a plurality of switching elements are arranged to apply input power for each row, and a plurality of switching elements are arranged to apply ground. Here, switching elements on an input power side and switching elements on a ground side may be turned on or off at the same time for each row so as to activate the GMR sensors. Accordingly, the GMR sensors may be sequentially activated.

Meanwhile, when the output terminals are connected in common for each row, the intensity of the magnetic field of a specific GMR sensor can be selectively measured.

In the first embodiment of the present invention, a case in which magnetic field vectors in the x-axis direction are detected will be described as an example. However, according to the first embodiment of the present invention, the second sensor array 200 may detect magnetic field vectors in the y-axis direction. For example, when the second sensor array 200 is rotated by 90 degrees on the x-y plane, magnetic field vectors in the y-axis direction may be detected.

The GMR sensor has omnipolar and hysteresis loop characteristics. Here, assuming that the GMR sensor has only the hysteresis loop characteristic, the output in the x-axis direction of the GMR sensor may be expressed by the following Equation 2 in a linear region:

$$V_X = C_1 \times p \times (1 - e^{-B_X^2}) + C_2 \quad (2)$$

where $C_1$ and $C_2$ are constants, p is drive voltage, and $B_X$ is the magnitude of the magnetic field in the x-axis direction.

According to this embodiment, the second sensor array 200 may obtain 3D magnetic field vectors by adding magnetic field vectors in the x-axis direction and magnetic field vectors in the y-axis direction to each other.

As described above, the sensor module according to the first embodiment of the present invention may measure both the distribution of a magnetic field in the x-axis direction and the distribution of the magnetic field in the z-axis direction, thereby being able to detect a crack in an object to be measured.

The operation of the apparatus for detecting a crack according to the embodiment of the present invention will now be described. When the switch control unit 20 supplies a control signal to the first input switch unit 120 and the second input switch unit 130, the first input switch unit 120 and the second input switch unit 130 are sequentially turned on and off and then the distribution of the magnetic field of an object to be measured in the z-axis direction is scanned. Furthermore, when the switch control unit 20 supplies a control signal to the input switch units of the second sensor array 200, the switch units are sequentially turned on and off and then the distribution of the magnetic field of the object to be measured in the x-axis direction is scanned. Accordingly, the apparatus for detecting a crack may analyze the distributions of the magnetic field of the object to be measured in the x- and z-axis directions in two dimensions.

Furthermore, when the second sensor array 200 is rotated by 90 degrees and then the same process is performed, the distributions of the magnetic field in the y- and z-axis directions may be analyzed in two dimensions.

Here, a signal processing unit may measure the 3D distribution of the magnetic field of the object to be measured by combining the two pieces of data, thereby being able to detect a crack.

Figure 5:
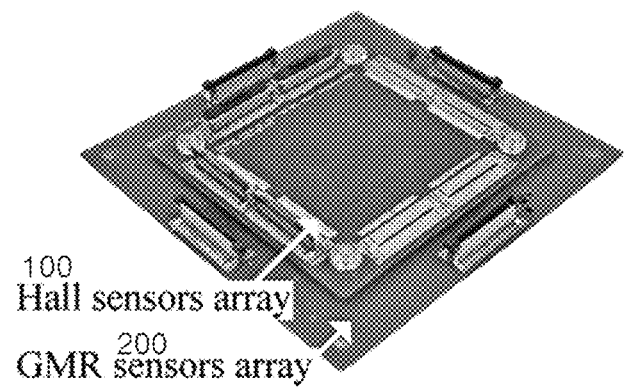
FIG. 5 is a photograph showing an actually manufactured product of the sensor module according to the first embodiment of the present invention.
Figure 6:
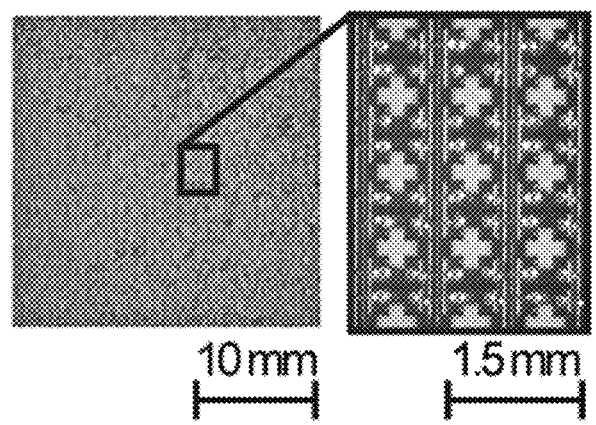
FIG. 6 is a photograph showing the first sensor array and an enlarged photograph showing part of the first sensor array.
Figure 7:
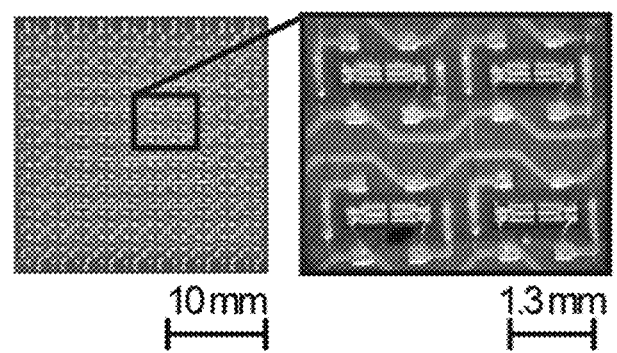
FIG. 7 is a photograph showing the second sensor array and an enlarged photograph showing part of the second sensor array.

FIG. 5 is a photograph showing an actually manufactured product of the sensor module according to the first embodiment of the present invention, FIG. 6 is a photograph showing the first sensor array and an enlarged photograph showing part of the first sensor array, and FIG. 7 is a photograph showing the second sensor array and an enlarged photograph showing part of the second sensor array.

As shown in FIGS. 5 to 7, the first sensor array 100 is formed by arranging 32×32 Hall sensors at intervals of 0.78 mm in two dimensions, and is fabricated using a semiconductor process. Furthermore, the second sensor array 200 is formed by arranging 6×6 GMR sensors in intervals of 2.34 mm in two dimensions, and is fabricated by separately mounting the GMR sensors on a printed circuit board (PCB) substrate.

Figure 8:
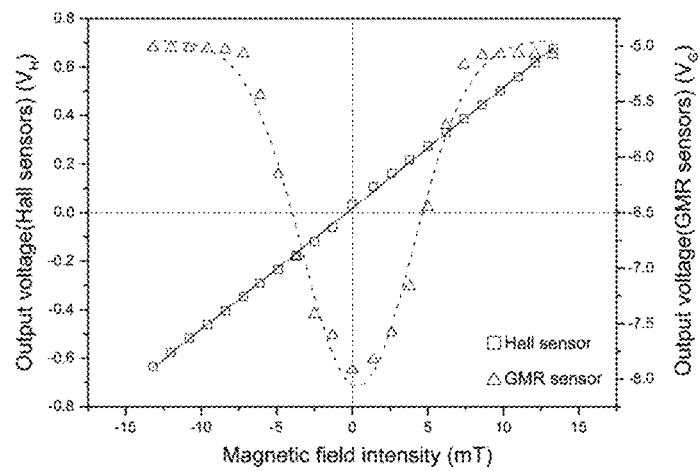
FIG. 8 is a graph showing the relationship between the intensity of an external magnetic field and output voltage.

FIG. 8 is a graph showing the relationship between the intensity of an external magnetic field and output voltage.

FIG. 8 is a graph showing voltages that were output when a magnetic field of ±13.3 mT was applied to the sensor module shown in FIG. 5 by applying a DC current of 5.5 A to a solenoid having a diameter of 230 mm and a length of 55 mm.

It can be noted from the results of the measurement that ±0.72 V was output in a region of ±13.3 mT in the first sensor array and linearity was maintained in the region. Furthermore, it can be noted that ±2.8 V was output in a region of ±13.3 mT in the second sensor array and linearity was maintained in the region.

The intensities of the magnetic field in the respective cases may be expressed by the following Equations 3 and 4:

$$V_H = C_{Z1} \times B_Z + C_{Z2} \quad (3)$$

where $V_H$ is voltage output from the first sensor array, $C_{Z1}$ and $C_{Z2}$ are constants, and $B_Z$ is the magnitude of the magnetic field in the z-axis direction (a vertical component);

$$V_G = C_{X1} \times B_X^2 + C_{X2} \times B_X + C_{X3} \quad (4)$$

where $V_G$ is voltage output from the second sensor array, $C_{X1}$, $C_{X2}$ and $C_{X3}$ are constants, and $B_X$ is the magnitude of a magnetic field in the x-axis direction (a lateral component). $V_G$ is always a positive number, and $B_X$ may have a positive or negative value.

Figure 9:
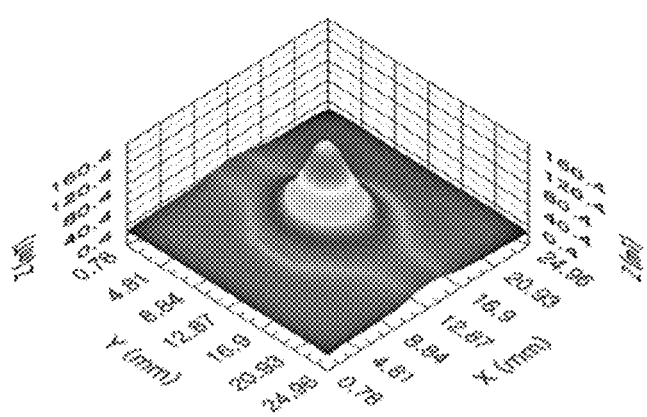
FIGS. 9 and 10 are graphs showing the magnetic field vectors of an Nd—Fe—B magnet having a diameter of 5 mm and a height of 3 mm that were measured using the sensor module shown in FIG. 5.
Figure 10:
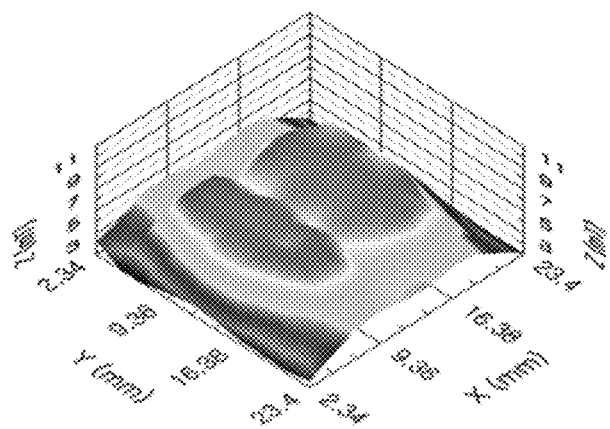

FIGS. 9 and 10 are graphs showing the magnetic field vectors of an Nd—Fe—B magnet having a diameter of 5 mm and a height of 3 mm that were measured using the sensor module shown in FIG. 5.

FIG. 9 shows the output of the first sensor array, and quantitatively shows the intensity of a magnetic field in the direction vertical to a sensor surface. FIG. 10 shows the output of the second sensor array, and quantitatively shows the intensity of the magnetic field in the x-axis direction lateral with respect to the sensor surface.

As shown in FIGS. 9 and 10, the sensor module according to the first embodiment of the present invention may quantitatively represent the distribution of a magnetic field.

Figure 11:
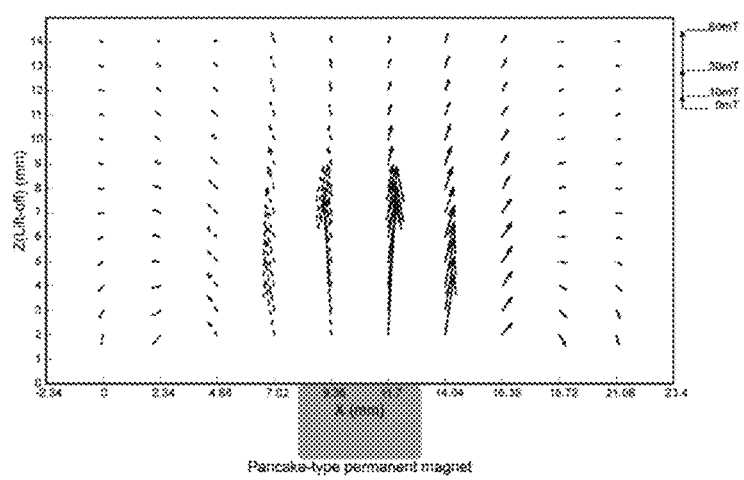
FIG. 11 is a graph showing the distribution of magnetic field vectors that were measured along the center line of a magnet using the sensor module of FIG. 5.

FIG. 11 is a graph showing the distribution of magnetic field vectors that was measured along the center line of the magnet using the sensor module of FIG. 5. In greater detail, FIG. 11 is a graph showing the distribution of magnetic field vectors along the center of a magnet on the x-z plane at lift-offs in the range from 2 to 14 mm.

FIG. 11 shows magnetic field vectors on the x-z plane. In FIG. 11, the dotted lines are used to indicate the possibility of negative values. These test results show that the distribution of the magnetic field vectors shown in FIG. 11 exhibits a tendency similar to that of the distribution of the magnetic field vectors of a permanent magnet.

FIGS. 12 to 15 are graphs showing the distribution of a magnetic field that was measured using the sensor module according to the first embodiment of the present invention after an artificial crack was formed in a magnetized ferromagnetic specimen near the center thereof.

In the test, the ferromagnetic specimen had dimensions of 100×200×5 mm. The artificial crack that was 1 mm wide, 10 mm long and 3 mm deep was formed in the specimen near the center thereof by electrical discharge machining (EDM). The specimen was magnetized and then magnetic field vectors leaked from the crack were measured. The lift-off was 1.2 mm.

Figure 12:
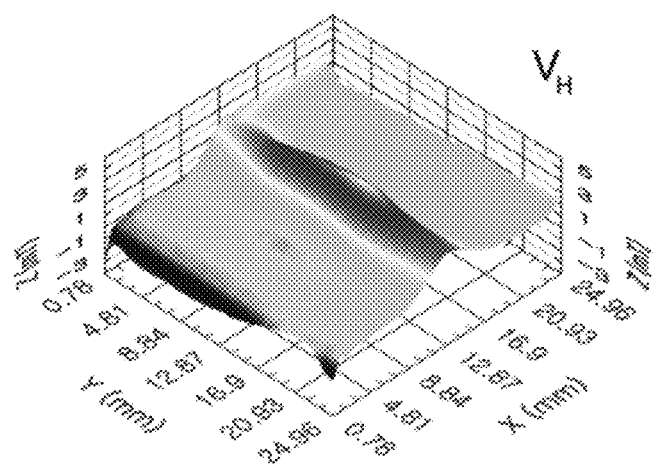
FIGS. 12 to 15 are graphs showing the distribution of a magnetic field that was measured using the sensor module according to the first embodiment of the present invention after an artificial crack was formed in a magnetized ferromagnetic specimen near the center thereof.
Figure 13:
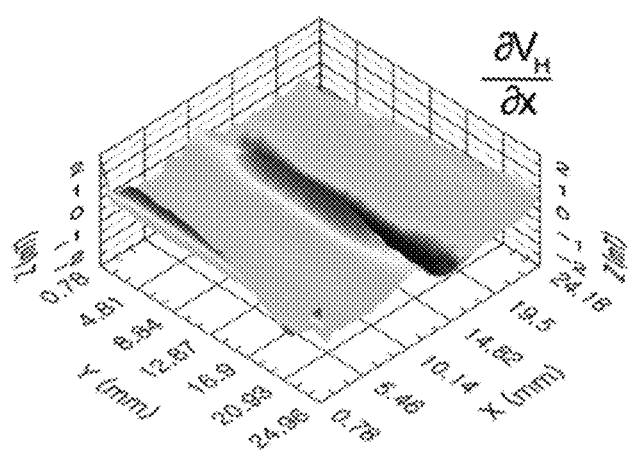

FIGS. 12 and 13 show the measurement of the distribution of the magnetic field that was output from the first sensor array, which was obtained by applying a gradient in the x-axis direction that is generated near the crack, measuring the distribution of the magnetic field in the z-axis direction, and then imaging leakage flux. The gradient in the x-axis direction results from the influence of a magnetizer.

Figure 14:
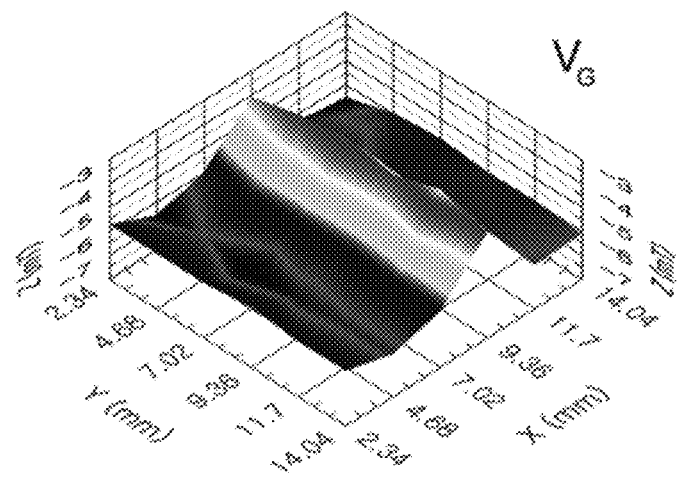
Figure 15:
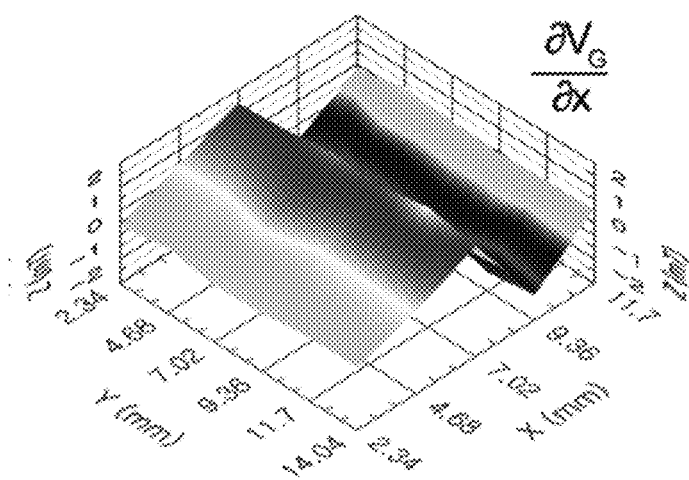

FIGS. 14 and 15 show the measurement of the distribution of the magnetic field that was output from the second sensor array, which was obtained by measuring the distribution of the magnetic field in the x-axis direction and imaging leakage flux.

As shown in FIGS. 3 to 15, the sensor module according to the first embodiment of the present invention can more accurately measure a crack in a object to be measured within a shorter period of time than the conventional technologies using the first sensor array capable of measuring the distribution of a magnetic field in the direction vertical to a sensor surface and the second sensor array capable of measuring the distribution of the magnetic field in the direction lateral with respect to the sensor surface.

Figure 16:
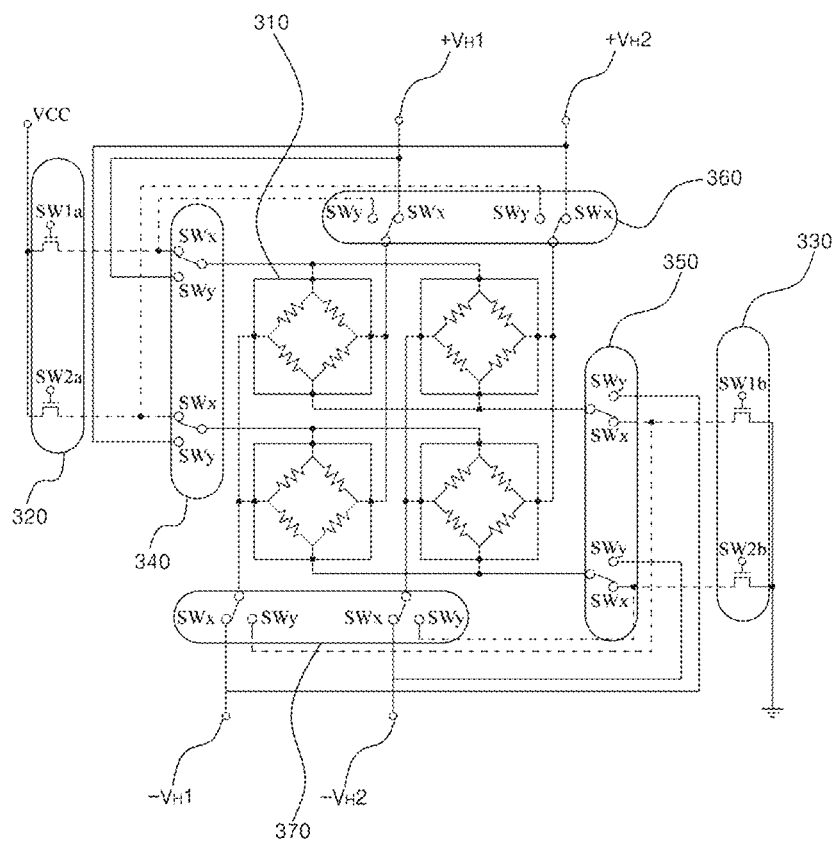
FIG. 16 is a circuit diagram showing the second sensor array of a sensor module according to a second embodiment of the present invention.

FIG. 16 is a circuit diagram showing the second sensor array of a sensor module according to a second embodiment of the present invention. The sensor module according to the second embodiment of the present invention may include a first sensor array and the second sensor array. The first sensor array is the same as shown in FIG. 3. The first sensor array measures the distribution of a magnetic field in the direction vertical to a sensor surface. Accordingly, the second sensor array will be described in detail below, with descriptions that are the same as those of the first sensor array being omitted.

Referring to FIG. 16, the second sensor array may include a plurality of magneto-resistive sensors 310, a third input switch unit 320, a fourth input switch unit 330, and first to fourth interchange switch units 340 to 370.

More specifically, a plurality of magneto-resistive sensors 310 may measure the distributions of a magnetic field in the x- and y-axis directions. For example, the magneto-resistive sensors 310 may be MR sensors. A case in which MR sensors are used will be described below. However, the magneto-resistive sensors are not limited thereto, but may be any type of sensors that are capable of measuring the distributions of a magnetic field in the x- and y-axis directions, like MR sensors.

The MR sensors 310 may be arranged in a matrix of O (a natural number) rows and O (a natural number) columns. Each of the MR sensors 310 includes two input terminals and two output terminals, and outputs voltages via the two output terminals because of its internal resistance when a magnetic field in the lateral direction is detected because of input power VCC and ground GND that are input to the two input terminals.

The third input switch unit 320 may selectively provide input power VCC to the MR sensors 310. The third input switch unit 320 may include a plurality of switching elements SW1a and SW2a in the column direction of an MR sensor array. Here, the number of switching elements SW1a and SW2a may be equal to the number of rows of the MR sensor array.

The fourth input switch unit 330 may selectively provide ground GND to the MR sensors 310.

The fourth input switch unit 330 may include a plurality of switching elements SW1b and SW2b in the column direction of the MR sensor array. Here, the number of switching elements SW1b and SW2b may be equal to the number of rows of the MR sensor array.

The third and fourth input switch units 320 and 330 may be the same as the first and second input switch units 120 and 130 shown in FIG. 3.

The first to fourth interchange switch units 340 to 370 are switched to interchange the first and second input terminals of the MR sensor 310 and the first and second output terminals thereof with each other. The first to fourth interchange switch units 340 to 370 use three-terminal switching elements, and allow input power VCC to be applied to the MR sensor 310 or allow the MR sensor 310 to output a high or low signal depending on the switching operation thereof.

For example, the first interchange switch unit 340 may include two three-terminal switching elements. The first terminal of each of the two three-terminal switching elements may be connected to a corresponding MR sensor 310, the second terminal thereof may be connected to the third input switch unit 320, and the third terminal thereof may be connected to an output terminal.

The second interchange switch unit 350 may include two three-terminal switching elements. The first terminal of each of the two three-terminal switching elements may be connected to a corresponding MR sensor 310, the second terminal thereof may be connected to the fourth input switch unit 330, and the third terminal thereof may be connected to the output terminal.

The third interchange switch unit 360 may also include two three-terminal switching elements. The first terminal of each of the two three-terminal switching elements may be connected to a corresponding MR sensor 310, the second terminal thereof may be connected to the third input switch unit 320, and the third terminal thereof may be connected to the output terminal.

The fourth interchange switch unit 370 may include two three-terminal switching elements. The first terminal of each of the two three-terminal switching elements may be connected to a corresponding MR sensor 310, the second terminal thereof may be connected to the fourth input switch unit 330, and the third terminal thereof may be connected to the output terminal.

Here, the second terminal of each of the switching elements of the first interchange switch unit 340 may be connected to the third terminal of a corresponding switching element of the third interchange switch unit 360, and the second terminal of each of the switching elements of second interchange switch unit 350 may be connected to the third terminal of a corresponding switching element of the third interchange switch unit 360.

Furthermore, the third terminal of each of the switching elements of the first interchange switch unit 340 may be connected to the second terminal of a corresponding switching element of the third interchange switch unit 360 or the output terminals of corresponding MR sensors 310, and the third terminal of each of the switching elements of the second interchange switch unit 350 may be connected to the second terminal of each of the switching elements of the fourth interchange switch unit 370 or the output terminals of corresponding MR sensors 310.

The number of switching elements of each of the first and second interchange switch units 340 and 350 may be equal to the number of MR sensors in each column. Furthermore, the number of switching elements of each of the third and fourth interchange switch units 350 and 360 may be equal to the number of MR sensors in each row. Accordingly, the input and output terminals are interchanged with each other by switching the directions of the switching elements, so that both the distributions of the magnetic field in the x- and y-axis directions can be measured.

For example, when all the MR sensors measure the distributions of an magnetic field in the x-axis direction, the switching elements of the first interchange switch unit 340 are switched to be connected to the third input switch unit 320 and the switching elements of the second interchange switch unit 350 are switched to be connected to the fourth input switch unit 330, as shown in FIG. 16. Furthermore, the switching elements of the third interchange switch unit 360 are switched to be connected to the output terminals of the MR sensors 310, and the switching elements of the fourth interchange switch unit 370 are switched to be connected to the output terminals of the MR sensors 310.

Here, when the switching elements of the third and fourth input switch units 330 are sequentially turned on and off, output values corresponding to the distributions of a magnetic field in the x-axis direction are output via the output terminals.

In contrast, when the distributions of the magnetic field in the y-axis direction are measured, the switching elements of the first and second interchange switch units 340 and 350 are switched such that the third terminals are connected to the output terminals of the MR sensors 310, the switching elements of the third interchange switch unit 360 are switched to be connected to the third input switch unit 320, and the switching elements of the fourth interchange switch unit 370 are switched to be connected to the fourth input switch unit 330.

As described above, the sensor module according to the second embodiment of the present invention may measure both the distribution of a magnetic field in the x-axis direction and the distribution of the magnetic field in the y-axis direction via the switching of the first to fourth interchange switch units 340 to 370 of the second sensor array 200.

Here, the switch control unit 20 that was described in conjunction with FIG. 1 may generate third and fourth control signals that control the switching elements of the third and fourth input switch units 330, and then supply the signals. Furthermore, the switch control unit 20 may generate a fifth control signal that controls the switching elements of the first to fourth interchange switch units 340 to 370, and then supply the signal.

Figure 17:
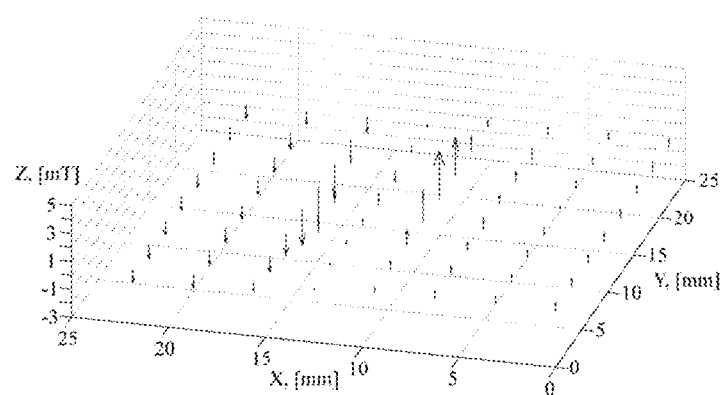
FIGS. 17 and 18 are graphs showing the distributions of magnetic fields that were measured using the apparatus for detecting a crack according to the embodiments of the present invention after artificial cracks having respective depths of 5 mm and 15 mm were formed in a magnetized ferromagnetic specimen.
Figure 18:
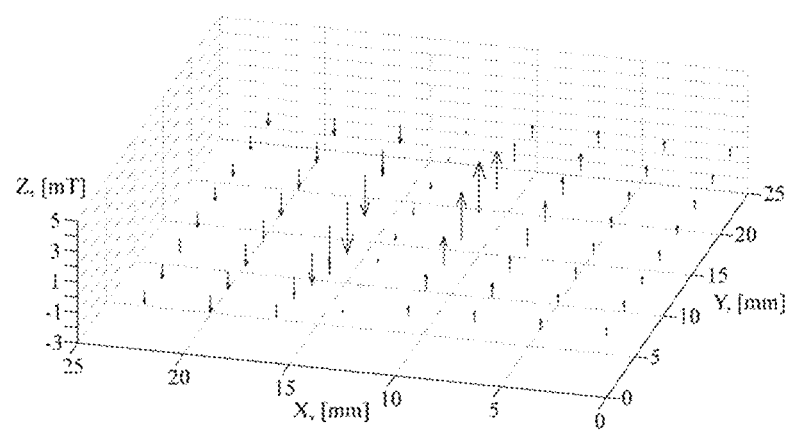

FIGS. 17 and 18 are graphs showing the distributions of magnetic fields that were measured using the apparatus for detecting a crack according to the embodiments of the present invention after artificial cracks having respective depths of 5 mm and 15 mm were formed in a magnetized ferromagnetic specimen.

From FIGS. 17 and 18, it can be seen that all the distributions of a magnetic field in the x-, y-, z-axis directions were measured.

Although the apparatus for detecting a crack according to the embodiments of the present invention has been described using the case in which GMR sensors and MR sensors are used in the second sensor array of the sensor module as examples, giant magneto-impedance (GMI) sensors, spin dependent tunneling (SDT) sensors, and magnetic tunnel junction (MTJ) sensors may be used instead of the GMR sensors and the MR sensors.

The apparatus for detecting a crack according to the embodiments of the present invention may be configured to use semiconductor switching elements, such as complementary metal-oxide semiconductors (CMOS), as the switching elements that are used in the first and second sensor arrays.

Furthermore, the apparatus for detecting a crack according to the embodiments of the present invention is configured such that the sensor array capable of measuring the distribution of a magnetic field in the z-axis direction of an object to be measured and the sensor array capable of measuring the distributions of the magnetic field on the x-y plane overlap each other in the vertical direction, thereby measuring a crack in the object to be measured in three dimensions.

Moreover, the apparatus for detecting a crack according to the embodiments of the present invention is configured to reduce the number of wires using a plurality of switching elements, thereby improving the level of integration.

The apparatus for detecting a crack according to the present invention has the advantage of measuring both the distribution of a magnetic field in the direction vertical to a sensor surface and the distribution of the magnetic field in the direction lateral with respect to the sensor surface.

Furthermore, the apparatus for detecting a crack according to the present invention has the advantage of reducing the number of input and output wires of the sensors using the switching elements capable of selectively supplying input and ground to the sensor arrays stacked in two layers, thereby increasing the number of sensors.

Furthermore, the apparatus for detecting a crack according to the present invention has the advantage of obtaining the 3D distribution of a magnetic field in such a way that the first sensor array measures the distribution of the magnetic field in the vertical direction and the second sensor array measures the distributions of the magnetic field in the x- and y-axis directions at the same time because the switching elements are provided such that the input and output terminals of the second sensor array can be interchanged with each other.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. An apparatus for detecting a crack, comprising:
   a power supply unit to supply power;
   a sensor module to receive the power from the power supply unit and to output detected signals corresponding to a magnetic field of an object to be measured, the sensor module comprising a first sensor array to detect magnetic field vectors in a direction vertical to a sensor surface and a second sensor array overlapped with the first sensor array to detect magnetic field vectors in a direction lateral with respect to the sensor surface, wherein the first sensor array comprises a plurality of magnetic sensors arranged in a matrix and each of the magnetic sensors comprises first and second input terminals to receive the power input from the power supply unit and first and second output terminals to output the detected signals;
   a signal receptor to convert the detected signals output from the sensor module into a quantitative value and compute a distribution of the magnetic field; and
   a first input switch unit arranged between the power supply unit and the first input terminal to selectively supply the power input from the power supply unit to the first input terminal; and a second input switch unit arranged between the second input terminal and the ground to selectively apply ground to the second input terminal, wherein the first and second input switch units are formed in a row direction, and each comprise switching elements whose number is equal to a number of magnetic sensors arranged in each row.

2. The apparatus of claim 1, wherein the first input switch unit comprises a plurality of switching elements, one terminal of each of which is connected to the first input terminals of the magnetic sensors arranged in a corresponding row, and the other terminal of each of which is connected to the power supply unit.

3. The apparatus of claim 1, wherein the second input switch unit comprises a plurality of switching elements, one terminal of each of which is connected to the second input terminals of the magnetic sensors arranged in a corresponding row and the other terminal of each of which is connected to the ground.

4. The apparatus of claim 1, further comprising a switch control unit to apply a first control signal that sequentially turns the plurality of switching elements of the first input switch unit on and off, and to apply a second control signal that sequentially turns the plurality of switching elements of the second input switch unit on and off.

5. The apparatus of claim 1, wherein the magnetic sensors are Hall sensors.

6. The apparatus of claim 1, wherein:
   the second sensor array comprises a plurality of magneto-resistive sensors arranged in a matrix; and
   each of the magneto-resistive sensors comprises first and second input terminals to receive the power input from the power supply unit and first and second output terminals to output the detected signals.

7. The apparatus of claim 1, wherein the signal receptor comprises an amplification unit to amplify output applied by the sensor module, a conversion unit to convert the output into a digital signal, or both of the amplification unit and the conversion unit.

8. The apparatus of claim 6, further comprising:
   a third input switch unit arranged between the power supply unit and the first input terminal of each of the magneto-resistive sensors to selectively supply the power input from the power supply unit to the first input terminal of each of the magneto-resistive sensors; and
   a fourth input switch unit arranged between the second input terminal and the ground to selectively apply ground to the second input terminal of each of the magneto-resistive sensors.

9. The apparatus of claim 8, wherein the third input switch unit comprises a plurality of switching elements, one terminal of each of which is connected to the first input terminals of the magneto-resistive sensors arranged in a corresponding row and the other terminal of each of which is connected to the power supply unit.

10. The apparatus of claim 8, wherein the fourth input switch unit comprises a plurality of switching elements, one terminal of each of which is connected to the second input terminals of the magneto-resistive sensors arranged in a corresponding row and the other terminal of each of which is connected to the ground.

11. The apparatus of claim 8, wherein the third and fourth input switch units are formed in a row direction, and each comprise switching elements whose number is equal to a number of magneto-resistive sensors arranged in each row.

12. The apparatus of claim 11, further comprising a switch control unit to apply a third control signal that sequentially turns the plurality of switching elements of the third input switch unit on and off, and to apply a fourth control signal that sequentially turns the plurality of switching elements of the fourth input switch unit on and off.

13. The apparatus of claim 12, wherein the switch control unit provides a fifth control signal that switches the switching elements of the first to fourth input switch units.

14. The apparatus of claim 8, further comprising a plurality of interchange switch units having first terminals thereof fixed to the magneto-resistive sensors, and to be switched to select second and third terminals, thereby interchanging the input and output terminals of the magneto-resistive sensors with each other;
   wherein the plurality of interchange switch units comprises:
   a first interchange switch unit having second terminals connected to the third input switch unit and third terminals connected to the first output terminals;
   a second interchange switch unit having second terminals connected to the fourth input switch unit and third terminals connected to the second output terminals;

a third interchange switch unit having second terminals connected to the first output terminals and third terminals connected to the third input switch unit; and a fourth interchange switch unit having second terminals connected to the second output terminals and third terminals connected to the fourth input switch unit.

15. The apparatus of claim 14, wherein:

when the switching elements of the first to fourth interchange switch units are switched to connect the first and second terminals with each other, the second sensor array measures a distribution of the magnetic field of the object to be measured in an x-axis direction; and when the switching elements of the first to fourth interchange switch units are switched to connect the first and third terminals with each other, the second sensor array measures a distribution of the magnetic field of the object to be measured in a y-axis direction.

16. The apparatus of claim 6, wherein each of the magneto-resistive sensors is independently selected from the group consisting of a magneto-resistive (MR) sensor, a giant magneto-resistive (GMR) sensor, a giant magneto-impedance (GMI) sensor, a spin dependent tunneling (SDT) sensor, and a magnetic tunnel junction (MTJ) sensor.

* * * * *